United States Patent [19]
Pettus

[11] Patent Number: 5,722,985
[45] Date of Patent: Mar. 3, 1998

[54] INSTRUMENT FOR TUMOR THERAPY

[76] Inventor: William G. Pettus, 194 Crane Dr., Monroe, Va. 24574

[21] Appl. No.: 774,888

[22] Filed: Dec. 27, 1996

[51] Int. Cl.⁶ ............................................. A61B 17/32
[52] U.S. Cl. .................................... 606/180; 606/170
[58] Field of Search .................................... 606/180, 171, 606/170, 167

[56] References Cited

U.S. PATENT DOCUMENTS 5,226,909  7/1993  Evans et al. ........................... 606/180

Primary Examiner—Michael Buiz
Assistant Examiner—Kevin Truong

[57] ABSTRACT

An instrument for treating deep malignant brain tumors. A slender conically-tipped yttrium tubular instrument is provided for simultaneous intra-tumor surgery, aspiration, and brachytherapy. Features include: minimally disruptive stereotactic access to the tumor, incremental rotary surgical excision from the center of the tumor, vacuum aspiration of excised matter and fluids through the tubular instrument, intense tumor-confined yttrium-90 beta radiation, and progressive suction collapsing of the tumor. Potential benefits include: tumor bulk reduction, relief of intracranial pressure, confined radiation of marginal tumor extensions, radiation sterilization of the instrument, prevention of seeding, and avoidance of radiation necrosis complications.

2 Claims, 1 Drawing Sheet

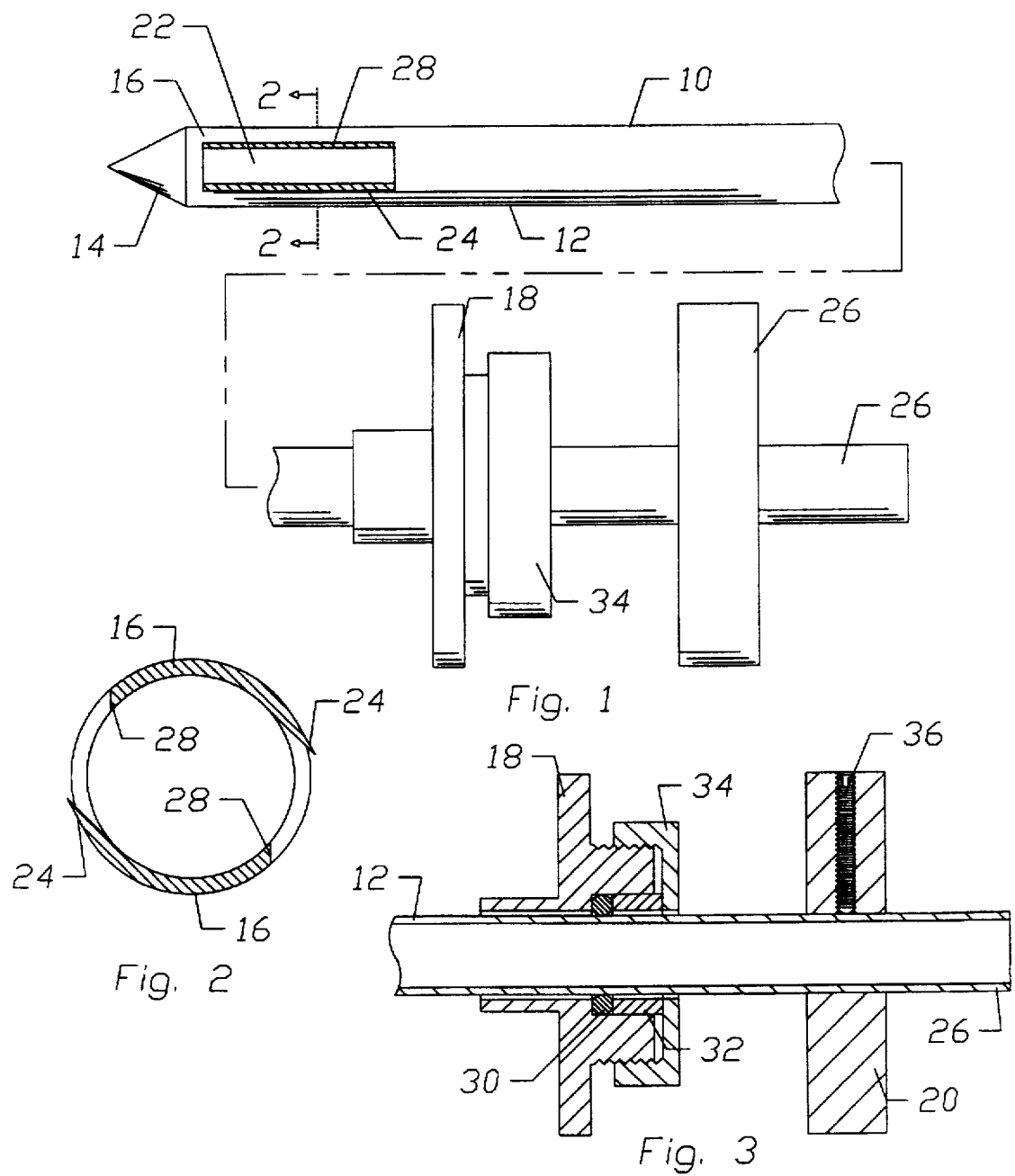

INSTRUMENT FOR TUMOR THERAPY

BACKGROUND OF THE INVENTION

1. Field of the Invention

The present invention is generally related to medical instruments and particularly to surgical, radiation, and aspiration instruments.

2. General Background

Deep malignant brain tumors are frequently inaccessible for conventional surgery and impossible to eradicate with safe doses of conventional radiation or with other conventional therapies. These tumors tend to become progressively debilitating due to the buildup of intracranial pressure and other complications, and most are fatal within a few years of detection. There is a need, therefore, for means of accessing deep brain tumors and eradicating or more effectively controlling these tumors.

SUMMARY OF THE INVENTION

The present invention addresses the above need in a unique manner that provides, in a single instrument, the simultaneous and synergistic benefits of stereotactic surgery, high energy beta brachytherapy, and aspiration, all administered from the center of the tumor. The instrument consists of a slender cone-tipped yttrium tube having a short activated section near the tip that provides an intense, highly localized radiation field in conjunction with surgical excision of tumor matter through longitudinal slots as the tube is reciprocally rotated. The open end of the tube is connected by a hose to a vacuum aspiration system that tends to decompress the cranium as it removes fluids and excised tumor fragments and collapses outlying tumor matter inward into the intense radiation field and into the surgical slots. Peripheral tumor extensions in normal brain tissue may also be extirpated by suction and eradicated as they are drawn inward into the radiation field. The progress of this operation is monitored by imaging techniques and analysis of aspirated tissue, and aspirator suction is reduced at the appropriate stage of tumor collapse to prevent significant radiation damage beyond the tumor margin and to control intracranial stress and the resulting strain in surrounding normal brain structures.

BRIEF DESCRIPTION OF THE DRAWINGS

For a further understanding of the nature and objects of the present invention, reference should be had to the following description, taken in conjunction with the accompanying drawings in which the parts are given like reference numerals, and wherein:

FIG. 1 is a side view of the instrument.

FIG. 2 is an enlarged cross section through segment 16, taken on line 2—2 of FIG. 1, illustrating the configuration of the cutting edges for rotary surgery.

FIG. 3 is an enlarged longitudinal section through the external fittings on tube 12.

DETAILED DESCRIPTION OF THE PREFERRED EMBODIMENT

Referring to the drawings, it may be seen in FIG. 1 that the invention is generally indicated by the numeral 10. Assembly 10 consists of: yttrium tube 12 with nominal dimensions of 4 mm outside diameter, 0.2 mm wall thickness, and 120 mm length, conical tip 14; surgical and radiation source segment 16 with two diametrically opposed longitudinal slots 22, nominally 2 mm wide and 10 to 20 mm long; flanged entrance fittings 18, 20, and 34 of stainless steel; and adjustable collar 20 of stainless steel.

As seen enlarged in FIG. 2, one side of each of slots 22 is beveled outward, raised slightly, and sharpened to form primary surgical edges 24 so as to excise or scoop tumor matter into slots 22 as tube 12 is rotated clockwise as viewed from its discharge end 26. The opposing secondary edges 28 of slots 22 are beveled inward and sharpened so as to complete the severing of tumor matter on the reciprocal counter-clockwise rotation of tube 12.

As seen in enlarged FIG. 3, fitting 18 houses rubber O-ring 30 compressed by stainless steel ring 32 through adjustment of stainless steel threaded cap 34 so as to restrict lateral movement of tube 12 and regulate the influx of air along the outer surface of tube 12. The inner surfaces of tube 12 may be Teflon coated. Collar 20, secured by set-screw 36, provides means of grasping and manipulating tube 12 and serves to limit the insertion of tube 12.

Prior to use, segment 16 of tube 12 is activated in a thermal neutron irradiation facility to provide a predetermined surface dose-rate up to about 1000 Gy/min of $^{90}Y$ beta radiation that has a 64 hour half-life, a maximum energy of 2.28 MeV, and a maximum range of about 11 mm in tissue. Immediately after activation, tube 12 is transported in a small shielding tube to the designated medical facility and stored for use before the beta activity has decayed below a predetermined level.

Other neutron-activated brachytherapy sources of beta or gamma radiation can be provided by fabricating tube 12 of iridium, gold, or other suitable metals, or by cladding tube 12 with these metals.

USE OF THE INVENTION

The general procedure for therapeutic use of the instrument is as follows: Burr hole 9 is prepared in skull 5 and entrance fitting 18 is inserted and secured to tissue 7 by adhesive means. Tube 12 is inserted into entrance fitting 18, and then stereotaxically inserted through the intervening normal brain tissue 3 and into the interior of tumor 1. During insertion, tube 12 is continuously rotated counterclockwise to avoid damage to normal tissue by raised surgical edges 24. O-ring bushing 30 in entrance fitting 18 is compressed by ring 32 through adjustment of threaded cap 34 to restrict lateral movement of tube 12 and to regulate the influx of air along the surface of tube 12. Collar 20 is adjusted and secured by set screw 36 so as to limit further insertion of tube 12 to a predetermined increment. The vacuum aspirator is then connected by a flexible hose to discharge end 26 of tube 12, and tube 12 is evacuated, causing tumor tissue to collapse into slots 22.

Collar 20 provides a means of grasping and manipulating tube 12 through cycles of surgical excision. Surgical edges 24 excise matter from the center of the tumor as tube 12 is instantaneously rotated 180 degrees clockwise and simultaneously advanced a few mm; edges 28 then complete the excision as tube 12 is rotated 180 degrees counter-clockwise and simultaneously retracted to its initial position. As this procedure is repeated, severed tumor fragments and fluids are removed by suction, severed blood vessels are cauterized by the intense beta radiation, and outlying regions of the tumor are collapsed onto segment 16 and into the region of intense radiation by the suction of the aspirator. Periodic interruption of the aspirator suction may be used to provide a pulsed impetus for propelling tumor matter through tube 12. When the surgery is terminated, any remaining marginal tumor tissue may be irradiated further until an optimal dose distribution has been achieved. Supplementary therapy, including radiation from special brachytherapy sources, radiosensitizers, chemotherapy, cryotherapy, and hyperthermia therapy, may then be administered through tube 12 if necessary. Tube 12 is then withdrawn with continuous counterclockwise rotation, entrance fitting 18 is removed, and appropriate post-surgical care is given.

What is claimed as invention is:

1. A device for brain tumor therapy comprising:

a. a conically tipped tubular member for simultaneous surgical excision, brachytherapy, and aspiration of matter from the interior of the tumor;

b. a longitudinal segment on a distal end of said tubular member adjoining the conical tip and having diametrically opposed longitudinal slots with surgically sharpened edges;

c. a neutron activated segment in said tubular member coincident with the longitudinally slotted segment;

d. a flanged entrance fitting with a compressible internal bushing, on a proximal end of said tubular member for laterally constraining said tubular member and for regulating the inward leakage of air along the outer surface of said tubular member;

e. an adjustable collar on the proximal end of said tubular member for grasping and manipulating said tubular member and for limiting the depth of insertion of said tubular member into the tumor.

2. The device of claim 1 wherein said tubular member comprises pure yttrium, $^{89}Y$.

* * * * *